United States Patent [19]

Weigert

[11] Patent Number: 4,814,522
[45] Date of Patent: Mar. 21, 1989

[54] CATALYTIC FLUOROOLEFIN TRANSHALOGENATIONS

[75] Inventor: Frank J. Weigert, Wilmington, Del.

[73] Assignee: E. I. DuPont DeNemours and Company, Wilmington, Del.

[21] Appl. No.: 143,203

[22] Filed: Jan. 11, 1988

Related U.S. Application Data

[63] Continuation of Ser. No. 858,101, May 6, 1986, abandoned, which is a continuation-in-part of Ser. No. 738,231, May 28, 1985, abandoned.

[51] Int. Cl.[4] ............ C07C 17/20; C07C 17/24; C07C 21/18; C07C 21/14
[52] U.S. Cl. .................... 570/160; 570/144; 570/153; 570/193; 570/216
[58] Field of Search ............ 570/153, 160, 144

[56]  References Cited

U.S. PATENT DOCUMENTS

| | | | |
|---|---|---|---|
| 2,478,201 | 8/1949 | Miller et al. | 260/653 |
| 2,478,932 | 8/1949 | Miller et al. | 260/653 |
| 2,637,748 | 5/1953 | Miller et al. | 260/653 |
| 2,676,996 | 4/1954 | Miller et al. | 260/653 |
| 2,694,739 | 11/1954 | Palthorp | 260/653 |
| 2,733,277 | 1/1956 | Miller | 570/163 |
| 2,767,227 | 10/1956 | Calfee et al. | 260/653 |
| 2,981,763 | 4/1961 | Neill et al. | 260/653.8 |
| 3,081,358 | 3/1963 | Agahegean et al. | 260/653.3 |
| 3,087,974 | 4/1963 | Hauptschein et al. | 260/653 |
| 3,087,975 | 4/1963 | Hauptschein et al. | 260/653 |
| 3,087,976 | 4/1963 | Hauptschein et al. | 260/653 |
| 3,138,559 | 6/1964 | Hauptschein et al. | 252/442 |
| 3,650,987 | 3/1972 | Vecchio et al. | 252/442 |
| 3,651,156 | 3/1972 | Scherer et al. | 260/653 |
| 3,787,331 | 1/1974 | Groppelli et al. | 252/442 |
| 3,793,229 | 2/1974 | Groppelli et al. | 252/442 |
| 3,878,257 | 4/1975 | Bruce | 260/653.4 |
| 4,069,266 | 11/1978 | Komatsu et al. | 260/653 |
| 4,192,822 | 3/1980 | Sweeney et al. | 260/653 |
| 4,734,503 | 3/1988 | Weigert | 570/144 |
| 4,748,284 | 5/1988 | Gozzo et al. | 570/151 |

FOREIGN PATENT DOCUMENTS

| | | | |
|---|---|---|---|
| 735974 | 6/1966 | Canada | 570/146 |
| 1618588 | 11/1978 | Fed. Rep. of Germany | |
| 117444 | 8/1974 | German Democratic Rep. | |
| 45-27748 | 11/1968 | Japan | |
| 6928 | 2/1985 | Japan | 570/163 |
| 555080 | 9/1975 | U.S.S.R. | |
| 636216 | 4/1976 | U.S.S.R. | |
| 999069 | 7/1965 | United Kingdom | 570/143 |
| 1369870 | 10/1974 | United Kingdom | |

OTHER PUBLICATIONS

Chem. Abstracts 82, 155162 (1975).
Information Disclosure Statement CR-8363, Ser. No. 738,231, filed May 28, 1985, dated 08-15-85.
Information Disclosure Statement CR-8363-A, Ser. No. 858,101, filed May 6,1986, dated Jul. 31, 1986.
Chem. Abstracts 85, 93718 (1976).
Chem. Abstracts 101, 130215 (1984).

Primary Examiner—J. E. Evans

[57]  ABSTRACT

Catalyzed halogen exchange between perhaloolefins to form products of the formulas:

$$R^1R^2C=CR^3R^8$$

and $$R^5R^6C=CR^7R^4$$

wherein $R^1$, $R^2$, $R^3$, $R^5$, $R^6$, and $R^7$ are individually selected from the group F, Cl, Br, $C_1$ to $C_4$ perfluoroalkyl, and pentafluorophenyl; or $R^1$ and $R^3$, $R^2$ and $R^3$, $R^5$ and $R^7$, $R^6$ and $R^7$ together, with the proviso that both groups are in the cis configuration, are selected from the group perfluoroalkylene of 2 to 4 carbons and $$o-C_6F_4(-)CF_2-,$$

$R^8=F$, $R^4=Cl$ or Br; and wherein none of the fluoroolefins simultaneously contains both Cl and Br.

7 Claims, No Drawings

CATALYTIC FLUOROOLEFIN TRANSHALOGENATIONS

RELATIONSHIP TO RELATED APPLICATIONS

This application is a continuation of application Ser. No. 858,101, filed May 6, 1986, which is a continuation-in-part of application Ser. No. 738,231, filed May 28, 1985, both now abandoned.

BACKGROUND OF THE INVENTION

This invention concerns transhalogenation between fluoroolefins. This type of exchange reaction, a special case of which is known as disproportionation, has been employed in the art primarily with chlorofluoroalkanes but not with fluoroolefins. One exception, U.S. Pat. No. 3,081,358, discloses the disproportionation of alkenes, specifically chloropentafluoropropenes, to hexafluoropropene and 1,1-dichlorotetrafluoropropene-1 in the presence of a specially prepared aluminum fluoride catalyst. The catalyst is not employed in the process of this invention.

A number of publications disclose the more common disproportionation of chlorofluoroalkanes. Those whcih use an alumina or aluminum fluoride catalyst include U.S. Pat. Nos. 3,087,976, 2,767,227, 2,637,748, 2,478,932, 2,676,996, and 2,478,201. Other catalysts have been employed in the disproportionation of alkanes include:

Alumina activated by pretreatment with a fluorochloroalkane or hexafluoropropene: U.S. Pat. Nos. 3,138,559, 3,087,975, and 3,087,974 and Japanese Pat. No. 43-27748;

Aluminum chloride on alumina: U.S. Pat. No. 2,694,739;

Aluminum fluoride which contains selected amounts of zinc, chromium, nickel and iron: U.S. Pat. Nos. 3,973,229, 3,787,331 and 3,650,987;

Chromiun oxide on activated carbon: E. German Pat. No. 117,444;

Zinc spinel: Russian Pat. No. 636,216;

Copper aluminate spinel: Russian Pat. No. 555,080;

Zirconium tetrachloride: *Chem. Abstracts* 101, 130215 (1984);

Zinc, cadmium and mercury: *Chem. Abstracts* 82, 155162 (1975);

Copper: *Chem. Abstracts* 85, 93718 (1976);

Activated carbon and chromium oxide: U.S. Pat. No. 4,192,822;

Aluminum fluoride which contains nickel and titanium: U.S. Pat. No. 4,069,266;

Chromium fluoride: U.S. Pat. No. 3,651,156;

Chromium oxyfluoride: G.B. Pat. No. 1,369,870;

Aluminum chloride: West German Pat. No. 1,618,588; and

Activated carbon: U.S. Pat. No. 2,981,763.

SUMMARY OF THE INVENTION

This invention concerns an improved process for continuously preparing by transhalogenation two fluoroolefins of the formula:

$R^1R^2C=CR^3R^8$ and $R^5R^6C=CR^7R^4$ which process comprises reacting at 100°–400° C. at a contact time of 0.001–10 seconds, a perhaloolefin of the formula:

$R^1R^2C=CR^3R^4$ with a perhaloolefin of the formula:

$R^5R^6C=CR^7R^8$ in the presence of a solid catalyst, as charged to the reactor, selected from the group consisting of:

A. chromium oxide alone or in combination with one or more of Rh°, Ru°, Ir°, Pd°, Pt°, Ag°, phosphorus oxide, silicon oxide, boron oxide or an oxide or halide of aluminum, manganese, zinc, iron, rhodium, nickel, palladium, cobalt, platinum, cerium, silver, copper, lead, bismuth, iridium, magnesium, barium, tin, lanthanum, calcium, ruthenium, iridium, zirconium, vanadium, molybdenum, or tungsten.

B. aluminum oxide in combination with one or more of Rh°, Ir°, Pd°, Pt°, Ag°, silicon oxide, phosphorus oxide, boron oxide or an oxide or halide of manganese, zinc, iron, rhodium, nickel, palladium, cobalt, platinum, cerium, silver, copper, lead, bismuth, iridium, magnesium, barium, tin, lanthanum, calcium, ruthenium, iridium, zirconium, vanadium, molybdenum, or tungsten.

wherein: $R^1$, $R^2$, $R^3$, $R^5$, $R^6$ and $R^7$ are individually selected from the group F, Cl, Br, $C_1$ to $C_4$ perfluoroalkyl, and pentafluorophenyl; or, $R^1$ and $R^3$ together or $R^2$ and $R^3$ together, or $R^5$ and $R^7$ together, or $R^6$ and $R^7$ together, can be selected, when both are in the cis position, from the group consisting of perfluoroalkylene of 2 to 4 carbons and $o-C_6F_4(-)CF_2-$, i.e.

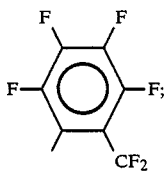

$R^8=F$, $R^4=Br$ or Cl; and wherein none of the reactants or products simultaneously contain both Cl and Br, and $R^1$, $R^2$, $R^3$, $R^4$, $R^5$, $R^6$, and $R^7$ may be chosen as to produce identical structures for the reactants or products.

DETAILED DESCRIPTION OF THE INVENTION

The present invention provides a process for transhalogenation of perhalogenated olefins which is characterized by lower process temperatures and increased throughput due to the greatly improved catalytic efficiency of the heterogeneous catalysts employed.

Transhalogenation can be represented by the reaction:

$R^1R^2C=CR^3R^4 + R^5R^6C=CR^7R^8 \rightleftharpoons R^1R^2C=CR^3R^8 + R^5R^6C=CR^7R^4$ $R^1$, $R^2$, $R^3$, $R^4$, $R^5$, $R^6$ and $R^7$ may be chosen such that both $R^1R^2C=CR^3R^4$ and $R^5R^6C=CR^7R^8$ are the same molecule. In this case when subjected to reaction conditions the molecule produces two distinct products for $R^1R^2C=CR^3R^8$ and $R^5R^6C=CR^7R^4$. This special case of transhalogenation is referred to as disproportionation. In addition $R^1$, $R^2$, $R^3$, $R^4$, $R^5$, $R^6$ and $R^7$ may be chosen such that both $R^1R^2C=CR^3R^4$ and $R^5R^6C=CR^7R^8$ represent two distinct molecules and when subjected to reaction conditions would produce identical structures for $R^1R^2C=CR^3R^8$ and $R^5R^6C=CF^7R^4$. This special case of transhalogenation is referred to as conproportionation. The following equations represent particular examples of disproportionation. The reverse are examples of conproportionation.

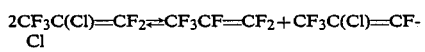

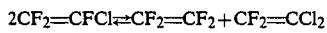

In each example of disproportionation, a perhaloolefin more highly fluorinated on the carbon-carbon double bond than the starting perhaloolefin is obtained. The coproduct obtained is correspondingly less fluorinated than the starting perhaloolefin. Subsequent recycle of the coproduct by fluorination by known methods, e.g., those disclosed in U.S. Pat. No. 3,878,257, will give the starting perhaloolefin which can be recycled in the disproportionation reaction. Thus, highly or completely fluorinated olefins can be readily obtained by the process of this invention.

As used throughout the specification, the terms "halo" and halide refer to F, Cl, and Br. Preferred fluoroolefin products are perfluoroolefins. Especially preferred perfluoroolefins are tetrafluoroethylene and hexafluoropropylene. Preferred perhaloolefin reactants are those which contain up to about 10 carbons, most preferably up to 6 carbons.

Transhalogenation Catalysts

Catalysts suitable for charging to the reactor in the process of the present invention are solid catalysts comprising supported metals, metal oxides or halides preferably selected from transition elements and rare earth elements. It is preferable that the chlorides, bromides and fluorides of the metal be relatively high melting, i.e., have a melting point above about 400° C. The melting points of such chlorides and fluorides are given by Glassner, U.S. government publication ANL-5750, "The Thermochemical Properties of the Oxides, Fluorides, and Chlorides to 2500° K.", Argonne National Laboratory.

Preferred catalysts are those that contain $Cr_2O_3$, supported on alumina or unsupported, and MnO on alumina. $Cr_2O_3$ is particularly preferred.

The term "oxide" and "halide" includes binary, ternary, quaternary, and higher polynary oxides and halides as well as solid solutions and non-stoichiometric oxides and halides. It includes a single oxide or halide; mixed oxides or halides of a single metal in different valence states such as FeO and $Fe_2O_3$, the corresponding chlorides, and the like; as well as mixed oxides or halides of different metals such as physical mixtures of iron oxide and manganese oxide, the corresponding chlorides, and the like. In the case of ruthenium, rhodium, iridium, palladium, platinum, and silver oxides and halides, the terms "oxide" and "halide" also refer to the products derived by calcination of such compounds, which can be the elemental forms of such metals, either singly or in combination with corresponding oxides and halides.

Representative catalysts of Group A include chromium sesquioxide ($Cr_2O_3$) alone or in combination with one or more of Rh°, Ru°, Ir°, Pd°, Pt°, Ag°, iron oxide, palladium fluoride, platinum chloride, cobalt oxide, nickel oxide, rhodium chloride, rhodium bromide, ruthenium chloride, iridium chloride, copper oxide, phosphorus pentoxide, boron oxide, barium oxide, lanthanum oxide, calcium oxide, zirconium oxide, cerium oxide, silver fluoride, copper oxide, copper chloride, manganese oxide, lead oxide, bismuth oxide, iridium chloride, magnesium oxide, silicone dioxide, tin oxide, vanadium oxide, molybdenum oxide or tungsten oxide.

Representative catalysts of Group B are aluminum oxide in combination with one or more of Rh°, Ru°, Ir°, Pd°, Pt°, Ag°, magnanese oxide, silicon dioxide, zinc oxide, zinc chloride, iron oxide, iron chloride, rhodium chloride, nickel chloride, nickel oxide, palladium oxide, palladium chloride, palladium fluoride, cobalt oxide, platinum chloride, platinum oxide, cerium oxide, silver fluoride, silver bromide, copper oxide, copper chloride, lead oxide, bismuth oxide, iridium chloride, phosphorus pentoxide, magnesium oxide, boron oxide, barium oxide, tin oxide, lanthanum oxide, calcium oxide, ruthenium oxide, iridium chloride, zirconium oxide, vanadium oxide, molybdenum oxide, or tungsten oxide.

Catalyst Preparation

The catalysts employed in the process of the present invention can be made by any conventional or suitable method in the art including evaporation, impregnation or precipitation, each followed by calcination. In the evaporation method, the desired components are mixed together with water to form a slurry or solution. The water is evaporated and the resultant solid is then dried and calcined. This method is of value where unwanted materials are not present and a washing step is not needed.

In the impregnation method, a solution of an active component or components is contacted with a support to thoroughly wet it. An excess of the impregnating solution is generally used and when the support is thoroughly saturated, the excess solution is removed, as by filtration or decantation. The impregnated support is then dried and subjected to calcination.

In the precipitation method, aqueous solutions of desired constituents are mixed with a solution of a precipitating agent. A variety of bases or base-forming compounds can be used as precipitating agents, including aqueous ammonia, ammonium carbonate, ammonium bicarbonate, urea and the like. The presence of impurities in the final catalyst is minimized by carrying out the precipitation with dilute solutions and by using ammonia or ammonium salts as the precipitant along with nitrates of the desired metals. The resulting precipitate then requires a minimum of washing since any absorbed material remaining can be removed in the subsequent calcination step.

In the calcination step which decomposes salts such as carbonate or nitrates to oxides, the catalyst material is heated in air to a temperature which is generally below 500° C. The calcination is usually carried out for several hours. The process of this invention is carried out in the gas phase using well-known chemical engineering practices, which include continuous, semi-continuous, and batch operation.

Preferably, the catalysts employed in the process of the present invention are activated prior to use. Activation can be achieved by preheating the catalyst at a relatively high temperature, e.g., about 300° to 400° C., with a fluoroolefin, for a period ranging from 1 minute to 1 hour. Activation is conveniently carried out in a flow system by passing the fluoroolefin over the catalyst contained in the reactor tube.

Specific fluoroolefins suitable for use in activation of the catalyst include tetrafluoroethylene, chlorotrifluoroethene, 1,1-dichloro-2,2-difluoroethane, hexafluoropropene, perfluoro-1-butene and perfluoro-2-butene. After activation, the catalysts can be efficiently employed at at temperatures as low as about 100° C.

It is not necessary that the catalyst have a high surface area. For instance, a $Cr_2O_3$ catalyst with a surface area as low as about 5 $m^2/g$ is suitable. It is preferred, however, that catalysts supported on alumina have a surface area greater than about 200 $m^2/g$.

Process Conditions

Preferred reaction temperatures are about 100° to 400° C. Pressures are about $10^{-3}$ to 10 MPa, preferably about 0.1 MPa. Contact times are preferably about 0.001 to 10 seconds.

It is preferred to operate a nonoxidative atmosphere in which molecular oxygen or similar oxidizing gases are absent. Generally, this results in fewer undesired by-products. The process is preferably carried out without any diluent but an inert atmosphere of nitrogen, helium, argon, neon, and the like can be used.

Contact time of the prehaloolefins with the catalyst can vary over a wide range depending upon reaction temperature, pressure, process dynamics, and the reactants and catalysts employed. For example, in a continuous flow process, a contact time as short as about 0.001 sec can be employed. Generally, longer contact times are employed at lower temperatures.

When a continuous flow process is employed, contact time is calculated using the following equation.

$$\text{Contact Time} = \frac{\text{Volume of Catalyst (mL)}}{\Sigma \text{Gas Flow Rates (mL/hr)}}$$

The transhalogenation process of the invention is conveniently carried out at atmospheric pressure, although either higher or lower pressures can be employed. The type of reactor vessel is not critical so long as it is able to withstand the temperatures and pressures employed. Corrosion resistant materials such as nickel-based corrosion resistant alloys (Hastelloy) and tantalum are preferred. The catalyst can be used in a fixed bed or a fluidized bed configuration.

After transhalogenation reaction has been completed, the reaction products can be separated by such conventional procedures as distillation, extraction by a solvent, adsorption, or other suitable techniques. Any portion of the starting perhaloolefins that is not reacted can be recycled.

EXAMPLES

The following Examples illustrate the invention. All parts and percentages are by weight, and all degrees are Celsius unless otherwise noted. Preferred embodiments are represented by Examples 63 and 64.

General Procedure

A designated quantity of catalyst was charged to a 1-cm diameter × 10-cm long glass reactor (Vycor®) which was heated in a tube furnace. When indicated, the catalyst was activated by heating at an elevated temperature for a designated time in a stream of hexafluoropropene. The reactor was then cooled to the temperature selected for reaction. Flow rates of gases were measured with a mass flow controller calibrated with tetrafluoroethylene. The feeds of perhaloolefins were started together with a feed of nitrogen is one was used. The product stream was transported directly to a gas chromatograph and analyzed on a 2.44 m × 0.32 cm (8' × ⅛") column of 1% of 20M molecular weight polyethylene glycol capped with nitroterephthalic acid on activated carbon, programmed as follows: 50° for 3 min; temperature raised at 20°/min to 150°; hold for 2 min; temperature raised at 35°/min to 200°; helium flow rate 20 mL/min. Product compositions are expressed in area percent with a flame ionization detector.

If transhalogenation was not observed at this initial reaction temperature, the temperature was raised until reaction was observed. If conversion of perhaloolefins was complete at the initial temperature, the temperature was lowered until partial conversion was obtained.

As used in the Examples, the following abbreviations for fluoroolefins and fluoroalkanes apply:

FC-114: 1,2-Dichlorotetrafluoroethane; $CF_2ClCF_2Cl$
FC-115: Chloropentafluoroethane; $ClCF_2CF_3$
FC-1110: Tetrachloroethane; $(Cl)_2C=C(Cl)_2$
FC-1111: Fluorotrichloroethane; $F(Cl)C=C(Cl)_2$
FC-1112a: 1,1-Dichloro-2,2-difluoroethene; $F_2C=C(Cl)_2$
FC-1112: 1,1-Dichloro-1,2-difluoroethene; $F(Cl)C=C(Cl)F$
FC-1113: Chlorotrifluoroethene; $CF(Cl)=CF_2$
FC-1114: Tetrafluoroethene; $CF_2=CF_2$
FC-216: 1,2-Dichlorohexafluoropropane; $CF_3CFClCF_2Cl$
FC-1211: 3-Fluoropentachloro-1-propene; $CFCl_2C(Cl)=CCl_2$
FC-1212: 3,3-Difluorotetrachloro-1-propene; $CF_2ClC(Cl)=CCl_2$
FC-1213: 1,1,2-Trichloro-3,3,3-trifluoro-1-propene; $CF_3C(Cl)=CCl_2$
FC-1214: 1,1-Dichloro-1,3,3,3-tetrafluoro-1-propene; $CF_3C(Cl)=CFCl$
FC-1215: 2-Chloropentafluoropropene; $CF_3C(Cl)=CF_2$
FC-1216: Hexafluoropropene; $CF_3CF=CF_2$ Catalyst Preparation Two general methods were used to prepare the catalysts used in the Examples: coevaporation and incipient wetness impregation.

Method A: Coevaporation

Each of the soluble inorganic salts was dissolved in water and the aqueous solutions were combined. The resulting solution was placed on a hot plate and the water was boiled off. The dry solid was then calcined in a furnace at 200° for 1 hr, and then at 400° for 1 hr. In the preparation of the catalyst of Example 38, 10% $CrF_3/Al_2O_3$, a solution of 73 g of hydrated aluminum nitrate, 3.7 g of hydrated chromium nitrate and 1 g of ammonium fluoride was heated to dryness, and the residue was calcined.

Method B. Impregnation

First, the pore volume of the support was determined by how much water could be absorbed into its pore structure. Then, a solution of the salt to be impregnated was dissolved in this calculated amount of water, and the solid support was added. The moist supported catalyst was calcined at 100° for 1 hr, at 200° for 1 hr. and finally at 400° for 1 hr. In the preparation of the catalyst, 10% $CrF_3/Cr_2O_3$, chromium oxide was found to adsorb 0.5 g of water/g of oxide. A solution of 0.5 g of ammonium fluoride in 2.5 mL of water was added to 5 g of $Cr_2O_3$. The solid catalyst was then calcined.

Catalyst preparations are summarized in Table 1. All preparations were by coevaporation except where noted by (B).

TABLE 1

| Catalyst Composition | Catalyst Composition |
|---|---|
| 10% $InCl_3/Al_2O_3$ | 2% $PdF_2/Al_2O_3$ |
| 10% $CrCl_3/Al_2O_3$ | 1% $CrF_3/Cr_2O_3$ |
| 2% $PdCl_2/Cr_2O_3$ | 10% $NiF_2/Al_2O_3$ |
| 20% $Ce_2O_3/Al_2O_3$ | 9% $CrF_3/Cr_2O_3$ |
| 20% $CoCl_2/Al_2O_3$ | 1% $NiF_2/Cr_2O_3$ |
| $Cr_2O_3$ | 3% $NiF_2/Cr_2O_3$ |
| 10% $MnO/Cr_2O_3$ | 9% $NiF_2/Cr_2O_3$ |
| 10% $Al_2O_3/Cr_2O_3$ | 10% $B_2O_3/Al_2O_3$ |
| 10% $CoO/Cr_2O_3$ | 20% $MgCl_2/Al_2O_3$ |
| 10% $Fe_2O_3/Cr_2O_3$ | 10% $P_2O_5/Cr_2O_3$ |
| 10% $NiO/Cr_2O_3$ | 10% $B_2O_3/Cr_2O_3$ |
| 1% $Pd/Cr_2O_3$ | 10% $CaCl_2/Cr_2O_3$ |
| 10% $CrF_3/Al_2O_3$ | 10% $BaO/Cr_2O_3$ |
| 10% $MnF_2/Al_2O_3$ | 10% $SnCl_2/Al_2O_3$ |
| 10% $CuF_2/Al_2O_3$ | 10% $ZnCl_2/Al_2O_3$ |
| 10% $FeF_3/Al_2O_3$ | 10% $La_2O_3/Al_2O_3$ |
| 10% $ZnF_2/Al_2O_3$ | 10% $La_2O_3/Cr_2O_3$ |
| 10% $CeF_3/Al_2O_3$ | 10% $ZrO_2/Cr_2O_3$ |
| 10% $CuO/Cr_2O_3$ | 10% $ZrO_2/Al_2O_3$ |
| 10% $MnO/Cr_2O_3$ | 10% $CaO/Cr_2O_3$ |
| 1% $Pd/Cr_2O_3$ | 10% $Cr_2O_3/Al_2O_3$—$SiO_2$ (B) |
| 10% $CoF_2/Al_2O_3$ | 10% $Cr_2O_3/TiO_2$—$Al_2O_3$ (B) |
| 3% $CrF_3/Cr_2O_3$ | 10% $Cr_2O_3/ZrO_2$ (B) |
| | 10% $CrF_3/Cr_2O_3$ (B) |

Comparative Experiment

In order to provide a standard against which the catalysts and processes of the present invention could be evaluated, a reaction substantially similar to those conducted as examples of the invention was conducted using $AlF_3$ as catalyst. The $AlF_3$ catalyst employed was a commercial catalyst marketed under the trade name Harshaw ® Al-1101.

A total of 8.0 g of $AlF_3$ catalyst was charged, and the reactor was heated to an initial temperature of 400°. Approximately equimolar streams of liquid FC-1213, 1 mL/hr, and gaseous FC-1216, 5 mL/min, and nitrogen (10 mL/min) were started, and the products were analyzed initially on the G.C. column, as follows: FC-1216, 46%; FC-1215, 0.9%; FC-1214, 2.9%; FC-1213, 47%.

Example 1

A total of 5.3 g of $Cr_2O_3$ catalyst (Newport Chrome) was charged, and the reactor was heated to an initial temperature of 350°. Approximately equimolar streams of liquid FC-1213, 1 mL/hr, and gaseous FC-1216, 5 mL/min, and nitrogen (20 mL/min) were started, and the products were analyzed initially on the G.C. column, as follows: FC-1216, 23%; FC-1215, 40%; FC-1214, 26%; FC-1213, 3%.

The reactor temperature was lowered progressively, and transhalogenation was continued. At 90°, with the same flow rates of FC-1213 and FC-1216 but with a nitrogen flow rate of 80 mL/min (calculated contact time of 0.7 sec), the product composition was 16% FC-1216; 35% FC-1215; 9% FC-1214; 39% FC-1213.

Examples 2 to 59

These Examples show a variety of catysts which can be employed in the transhalogenation reaction:

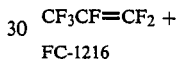

FC-1216

FC-1213      FC-1214      FC-1215

The reactions were carried out by the General Procedure set forth above, with the following additional qualifications. Feed rates of 1 mL/hr of liquid FC-1213 and 5 mL/min of gaseous FC-1216 were used. Examples 2 to 4 used a nitrogen stream of 10 mL/min, and in Examples 5 to 32 and 40 to 42 a stream of nitrogen of 5 mL/min was used. No nitrogen was used in Examples 33 to 39 and 43 to 59. The catalysts used in Examples 12 to 59 were activated by pretreatment with a stream of FC-1216 (5 mL/min) at 400° for 15 min (Examples 12 to 14) or 10 min (Examples 15 to 59). The specific catysts used, initial temperatures ($T_i$), reaction temperatures ($T_r$), and product compositions are summarized in Table 2, below.

TABLE 2

| | | Temperature | Product Analysis | | | |
|---|---|---|---|---|---|---|
| Ex. | Catalyst, g | $T_i/T_r$ (°C.) | FC-1216 | FC-1215 | FC-1214 | FC-1213 |
| 2 | 57% $MgO/Al_2O_3$, 4.7 | 300/400 | 32 | 20 | 14 | 32 |
| 3 | 19% $Cr_2O_3/Al_2O_3$, 7.6 | 400/200 | 17 | 34 | 23 | 26 |
| 4 | 33% Cr/Si—Al/O, 5.0 | 400/200 | 19 | 42 | 31 | 9 |
| 5 | 3% each of Ni,Co, Fe oxides/$Al_2O_3$, 7.0 | 300/250 | 29 | 35 | 14 | 22 |
| 6 | 20% $FeO/Al_2O_3$ | 300/200 | 39 | 20 | 4 | 36 |
| 7 | 14% $NiO/Al_2O_3$, 5.0 | 300/200 | 36 | 22 | 10 | 32 |
| 8 | 20% $FeCl_3/Al_2O_3$, 5.0 | 300/200 | 24 | 39 | 26 | 8 |
| 9 | 10% $MoO_3/Al_2O_3$, 5.0 | 300/300 | 47 | 28 | 16 | 7 |
| 10 | 10% $WO_3/Al_2O_3$, 7.0 | 300/300 | 45 | 25 | 7 | 3 |
| 11 | 10% $MnO/Al_2O_3$, 5.8 | 300/200 | 45 | 14 | 9 | 30 |
| 12 | 10% $InCl_3/Al_2O_3$, 2.5 | 300/200 | 32 | 24 | 8 | 31 |
| 13 | 0.5% $Pt/Al_2O_3$, 5.0 | 300/200 | 35 | 15 | 3 | 38 |
| 14 | 0.5% $Pd/Al_2O_3$, 5.0 | 300/200 | 40 | 10 | 2 | 39 |
| 15 | 10% each $ZnO/Cr_2O_3/Al_2O_3$, 5.0 | 300/200 | 18 | 34 | 25 | 11 |
| 16 | 1% $FeO/Cr_2O_3$, 2.0 | 150/150 | 31 | 32 | 10 | 26 |

TABLE 2-continued

| Ex. | Catalyst, g | Temperature $T_i/T_r$ (°C.) | Product Analysis | | | |
|---|---|---|---|---|---|---|
| | | | FC-1216 | FC-1215 | FC-1214 | FC-1213 |
| 17 | 1% PdCl$_2$/Cr$_2$O$_3$, 2.0 | 150/250 | 44 | 4 | 11 | 38 |
| 18 | 1% Pt/Cr$_2$O$_3$, 2.0 | 150/150 | 41 | 11 | 4 | 43 |
| 19 | 1% CoCl$_2$/Cr$_2$O$_3$, 2.0 | 150/150 | 33 | 5 | 1 | 61 |
| 20 | 20% CoCl$_2$/Al$_2$O$_3$, 2.0 | 150/200 | 39 | 20 | 6 | 35 |
| 21 | 20% Ce$_2$O$_3$/Al$_2$O$_3$, 2.0 | 150/300 | 49 | 8 | 2 | 40 |
| 22 | 24% ZnO/Al$_2$O$_3$, 5.0 | 150/300 | 47 | 10 | 2 | 40 |
| 23 | 10% Ag/Al$_2$O$_3$, 2.0 | 150/300 | 45 | 13 | 8 | 33 |
| 24 | 10% CrCl$_3$/Al$_2$O$_3$, 1.0 | 150/300 | 30 | 32 | 17 | 21 |
| 25 | 10% Al$_2$O$_3$/Cr$_2$O$_3$, 1.0 | 200/300 | 24 | 31 | 18 | 23 |
| 26 | 10% NiO/Cr$_2$O$_3$, 1.0 | 200/200 | 17 | 42 | 29 | 12 |
| 27 | 10% CoO/Cr$_2$O$_3$, 1.0 | 200/200 | 45 | 12 | 2 | 4 |
| 28 | 10% Fe$_2$O$_3$/Cr$_2$O$_3$, 1.0 | 200/300 | 23 | 31 | 26 | 19 |
| 29 | 10% FeF$_3$/Al$_2$O$_3$, 2.0 | 300/300 | 31 | 40 | 19 | 10 |
| 30 | 10% CuF/Al$_2$O$_3$, 2.0 | 300/300 | 51 | 10 | 3 | 35 |
| 31 | 10% ZnF$_2$/Al$_2$O$_3$, 2.0 | 300/300 | 40 | 34 | 17 | 3 |
| 32 | 10% CeF$_3$/Al$_2$O$_3$, 2.0 | 300/300 | 65 | 20 | 6 | 5 |
| 33 | 10% MnF$_2$/Al$_2$O$_3$, 2.0 | 300/300 | 13 | 26 | 34 | 21 |
| 34 | 10% NiF$_2$/Al$_2$O$_3$, 2.0 | 300/300 | 19 | 38 | 29 | 10 |
| 35 | 2% PdF$_2$/Al$_2$O$_3$, 2.0 | 300/300 | 33 | 26 | 17 | 19 |
| 36 | 10% CuO/Cr$_2$O$_3$, 1.0 | 200/300 | 27 | 46 | 23 | 4 |
| 37 | 10% CrF$_2$/Al$_2$O$_3$, 2.0 | 300/300 | 63 | 22 | 3 | 10 |
| 38 | 9% CrF$_3$/Cr$_2$O$_3$, 2.0 | 300/300 | 15 | 45 | 33 | 7 |
| 39 | 3% CrF$_3$/Cr$_2$O$_3$, 2.0 | 300/150 | 18 | 44 | 21 | 17 |
| 40 | 3% NiO/Cr$_2$O$_3$, 1.0 | 200/300 | 16 | 41 | 28 | 15 |
| 41 | 9% NiO/Cr$_2$O$_3$, 1.0 | 200/200 | 12 | 45 | 36 | 6 |
| 42 | 10% CoF$_2$/Al$_2$O$_3$, 2.0 | 300/300 | 20 | 41 | 32 | 6 |
| 43 | 10% PbO/Al$_2$O$_3$, 2.0 | 300/300 | 25 | 28 | 21 | 26 |
| 44 | 10% Bi$_2$O$_3$/Al$_2$O$_3$, 2.0 | 300/300 | 24 | 29 | 24 | 22 |
| 45 | 10% P$_2$O$_5$/Cr$_2$O$_3$, 2.0 | 300/200 | 13 | 41 | 36 | 10 |
| 46 | 20% MgCl$_2$/Al$_2$O$_3$, 2.0 | 300/300 | 47 | 5 | 1.4 | 45 |
| 47 | 10% B$_2$O$_3$/Al$_2$O$_3$, 2.0 | 300/300 | 47 | 3 | 2 | 47 |
| 48 | 10% B$_2$O$_3$/Cr$_2$O$_3$, 2.0 | 300/200 | 9 | 41 | 42 | 7 |
| 49 | 10% BaO/Cr$_2$O$_3$, 1.0 | 300/300 | 10 | 40 | 38 | 11 |
| 50 | 10% SnCl$_2$/Al$_2$O$_3$, 3.0 | 300/300 | 47 | 7 | 3 | 42 |
| 51 | 10% ZnCl$_2$/Al$_2$O$_3$, 3.0 | 300/300 | 22 | 41 | 19 | 17 |
| 52 | 10% La$_2$O$_3$/Al$_2$O$_3$, 3.0 | 300/300 | 42 | 14 | 7 | 36 |
| 53 | 10% La$_2$O$_3$/Cr$_2$O$_3$, 2.0 | 300/300 | 11 | 44 | 39 | 6 |
| 54 | 10% CaO/Cr$_2$O$_3$, 2.0 | 300/300 | 41 | 14 | 8 | 36 |
| 55 | 91% SiO$_2$/Al$_2$O$_3$, 5.0 | 300/300 | 56 | 10 | 2 | 28 |
| 56 | 10% Cr$_2$O$_3$/Si—Al—O, 4.0 | 300/300 | 8 | 37 | 44 | 8 |
| 57 | 98% ZrO$_2$/Al$_2$O$_3$, 5.0 | 300/300 | 63 | 4 | — | 28 |
| 58 | Cr—Y Zeolite, 3.0 | 300/300 | 21 | 42 | 22 | 14 |
| 59 | 10% ZrO$_2$/Cr$_2$O$_3$, 3.0 | 300/400 | 39 | 12 | 5.4 | 41 |

Example 60

Tetrafluoroethylene+FC 1213. Reaction was carried out by the General Procedure using 5 g of the Cr$_2$O$_3$ catalyst of Example 1, 5 mL/min of gaseous tetrafluoroethylene (TFE), 0.5 mL/hr of liquid FC-1213, and 20 mL/min of nitrogen. The initial reaction temperature was 100° and the temperature was raised eventually to 250°. Reaction started at 100°. At 150°, the product composition was 23% TFE, 21% chlorotrifluoroethene, 30% FC-1215, 15% dichlorodifluoroethene, 5% FC-1214, and 3% FC-1213.

Example 61

Disproportionation of Chlorotrifluoroethene. Reaction was carried out by the General Procedure using 7 g of the Cr$_2$O$_3$ catalyst of Example 1, 5 mL/min of gaseous chlorotrifluoroethene, and 20 mL/min of nitrogen. The initial temperature was 150°. At 250°, the product composition was 8% TFE, 72% chlorotrifluoroethene, and 13% dichlorodifluoroethene.

Example 62

Disproportionation of FC-1214. Reaction was carried out by the General Procedure using 8 g of the Cr$_2$O$_3$ catalyst of Example 1, 0.5 mL/hr of liquid FC-1214 (with cooling of the syringe), and 20 mL/min of nitrogen. The initial temperature was 100°. At 200°, the product composition was 67% FC-1214, 11% FC-1213, 21% FC-1215, and 0.6% FC-1216.

Example 63

Disproportionation of FC-1215. Reaction was carried out by the General Procedure using 5 g of Cr$_2$O$_3$ catalyst, 4 mL/min of gaseous FC-1215, and 10 mL/min of nitrogen. The initial temperature was 250°. At 100° and 20 mL/min of nitrogen, the product composition was 17% FC-1216, 55% FC-1215, 23% FC-1214, and 5% FC-1213.

Example 64

Disproportionation of Chlorotrifluoroethene. Reaction was carried out by the General Procedure using 15 g of Cr$_2$O$_3$ catalyst, 5 mL/min of nitrogen, and 5 mL/min of chlorotrifluoroethene at various temperatures. The results are summarized in Table 3, below, in which the products are shown in area percent as determined by GC/MS. Disproportionation was reasonably complete at 180° to give FC-1114 (CF$_2$=CF$_2$) and FC-1112 (CF$_2$=CCl$_2$).

TABLE 3

| Temp (°C.) | Product Analysis | | | | | |
|---|---|---|---|---|---|---|
| | FC-1114 | FC-115 | FC-1113 | FC-1112a | FC-1112 | FC-1111 |
| 180 | 17 | 0.8 | 58 | 9.5 | 11.8 | 1.2 |

TABLE 3-continued

| Temp (°C.) | Product Analysis |  |  |  |  |  |
|---|---|---|---|---|---|---|
|  | FC-1114 | FC-115 | FC-1113 | FC-1112a | FC-1112 | FC-1111 |
| 200 | 18 | 1.2 | 56 | 10 | 12 | 1.4 |
| 230 | 15 | 9.9 | 37 | 20 | 7 | 3.1 |
| 250 | 11 | 18 | 25 | 28 | 4 | 5 |

Example 65

Disproportionation of 1-Bromo-1,2,2-trifluoroethene. Reaction was carried out by the General Procedure using 5 g of $Cr_2O_3$ catalyst, 5 mL/min of gaseous 1-bromo-1,2,2-trifluoroethene, and 5 mL/min of nitrogen. The initial temperature was 250°. At 300°, the product composition was shown to contain $CF_2\!=\!CBr_2$ by nmr analysis. GC analysis of the gas stream on-line showed 3 assignable peaks: FC-1114 (9.7 area %); $CF_2\!=\!CFBr$ (32 area %); and $CF_2\!=\!CBr_2$ (32 area %). Small amounts of perhaloalkanes were seen in both the GC and NMR.

Example 66

TFE + 1,1-Dichloro-2,2-difluoroethene. Reaction was carried out by the General Procedure using 10 g of $Cr_2O_3$ catalyst and the designated amounts of gaseous TFE and gaseous 1,1-dichloro-2,2-difluoroethene. The initial temperature was 275°. Reaction products are summarized in Table 4, below.

TABLE 4

| Temp. (°C.) | Feed Rate mL/min | | Product Analysis FC- | | | | | |
|---|---|---|---|---|---|---|---|---|
|  | 1114 | 1112 | 1114 | 115 | 1113 | 114 | 1112 | 1111 |
| 275 | 5 | 5 | 7.1 | 12.2 | 10.6 | 7.7 | 33 | 5.7 |
| 275 | 6 | 4 | 16.5 | 8 | 9.8 | 9.3 | 29 | 5.3 |
| 275 | 4 | 6 | 14.4 | 5 | 7 | 7 | 41 | 8.2 |
| 300 | 5 | 5 | 9.6 | 9.4 | 16.3 | 7.2 | 33 | 6.4 |
| 250 | 5 | 5 | 29 | 2.0 | 11.4 | 3.3 | 44 | 4.3 |

Example 67

TFE + 1,2-Dichloro-1,2-difluoroethene. The procedure of Example 66 was employed except that 1,1-dichloro-2,2-difluoroethene was replaced with 1,2-dichloro-1,2-difluoroethene (5 mL/min). The inital temperature was 275°. GC analysis showed the following principal products. Area percents are noted in parentheses: FC-114 (26); FC-115 (9.6); FC-1113 (31); FC-114 (12.3); FC-1112 (10.6); FC-1111 (0.9).

Example 68

FC-1216 + Tetrachloroethene. Reaction was carried out by the General Procedure using 5 g of $Cr_2O_3$ catalyst, activated by heating in a stream FC-1216 (5 mL/min) at 100° for 0.5 hr. Nitrogen (5 mL/min) and liquid tetrachlorethene (5 mL/hr) streams were started. After 0.5 hr, the temperature was raised to 400°. The results obtained at several temperatures are summarized in Table 5, below.

TABLE 5

| Temp | FC-1216 | FC-1215 | FC-1214 | FC-1112 | FC-1111 | FC-1110 |
|---|---|---|---|---|---|---|
| 400 | 24 | 11 | 3 | 1.4 | 5.3 | 54 |
| 400(1) | 14 | 6.5 | 2.2 | 1.3 | 4.8 | 70 |
| 400(2) | 70 | 13 | 1.6 | 1.6 | 1.8 | 11 |
| 300(3) | 45 | 16 | 15 | 1.7 | 1.3 | 14.4 |
| 350(1) | 22 | 12 | 4 | 2.7 | 4.2 | 48 |

(1) Tetrachloroethene flow rate was 1.5 mL/hr
(2) Tetrachloroethene flow rate was 0.6 mL/hr
(3) FC-1216, 10 mL/min; tetrachloroethene, 1 mL/hr

Example 69

1,1-Dichloro-2,2-difluoroethene + Tetrachloroethene. Reaction was carried out by the General Procedure using 10 g of $Cr_2O_3$ catalyst with no activation. Nitrogen (5 ml/min), liquid tetrachloroethane (1 ml/hr), and gaseous 1,1-dichloro-2,2-difluoroetheene (7 to 10 ml/min) were passed over the catalyst at 330°. The principal product formed was fluorotrichloroethene.

Example 70

FC-1213 + Octafluoro-2-butene. Reaction was carried out by the General Procedure using 5 g of $Cr_2O_3$ catalyst activated by heating in a stream of gaseous octafluoro-2-butene (5 ml/min) at 400° for 10 min. The reactor temperature was lowered to 300°, and a stream of liquid FC-1213 (1 mL/hr) was started. The temperature was lowered to 200° and the product stream was analyzed. NMR analysis of the product showed the presence of FC-1213, FC-1214, and FC-1215 in the molar ratio of 60:21:18. Both perfluoro-cis- and perfluoro-trans-2-butene were present as well as the corresponding compounds with one or both or the vinyl fluorines replaced by chlorine, i.e. $CF_3CF\!=\!C(Cl)CF_3$ and $CF_3C(Cl)\!=\!C(Cl)CF_3$. The ratio of butenes with 2:1:0 chlorine atoms was 31:29:31.

Example 71

FC-1213 + Hexafluorocyclobutene. Reaction was carried out by the General Procedure using 5 g of $Cr_2O_3$ catalyst, activated by heating in a stream of gaseous hexafluorocyclobutene (5 mL/min) at 400° for 10 min. The reactor temperature was lowered to 300°, and a stream of liquid FC-1213 (1 mL/hr) was started. The reaction temperature was lowered to 200°, and a liquid sample was collected and analyzed by NMR. The following products were identified: FC-1213, FC-1214, and FC-1215 in the molar ratio of 41:22:37; hexafluorocyclobutene, 1-chloropentafluorocyclobutene, and 1,2-dichlorotetrafluorocyclobutene in the molar ratio of 8:39:54.

Example 72

FC-1213 + Octafluorocyclopentene. Reaction was carried out by the General Procedure using 5 g of $Cr_2O_3$ catalyst, activated by heating in a stream of gaseous octafluorocyclopentene (5 mL/min) at 400° for 10 min. The reactor temperature was lowered to 300°, and a stream of liquid FC-1213 (1 mL/hr) was started. The reaction product was analyzed by fluorine nmr. The following products were identified: equimolar amounts of FC-1213, FC-1214, and FC-1215; equimoar amounts of octafluorocyclopentene, 1-chloroheptafluorocyclopentene, and 1,2-dichlorohexafluorocyclopentene.

Example 73

FC-1213 + Perfluoro-4-methyl-2-pentene. Reaction was carried out by the General Procedure using 5 g of $Cr_2O_3$ catalyst, activated by heating in a stream of gaseous FC-1216 (5 mL/min) and nitrogen (5 mL/min) at 400° for 10 min. The reactor temperature was lowered to 300° and the FC-1216 stream was discontinued. A stream of liquid (1 mL/hr) consisting of an equimolar mixture of FC-1213 and perfluoro-4-methyl-2-pentene was started. GC/MS showed the presence of 4 isomers of $C_6F_{11}Cl$ and NMR showed the presence of FC-1213, FC-1214, and FC-1215 in the molar ratio of 12:5:1.

I claim:

1. A process for exchanging a fluorine atom from one perhaloolefin for a chlorine or bromine atom from another perhaloolefin, which comprises contacting at 90°–400° C., for a contact time of 0.001–10 seconds, a perhaloolefin of the formula

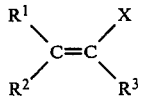

and a perhaloolefin of the formula

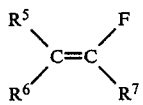

to form the perhaloolefins

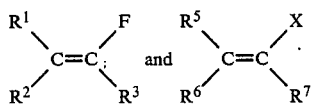

wherein

X is bromine or chlorine, $R^1$, $R^2$, $R^3$, $R^5$, $R^6$ and $R^7$ when each is taken individually is selected from the class consisting of F, Cl, Br, perfluoroalkyl of 1 to 4 carbon atoms, and pentafluorophenyl; and the pairs $R^2$ and $R^3$, and, $R^6$ and $R^7$, when each pair is taken together, is selected from the class consisting of

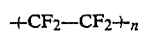

where n=1 or 2 and

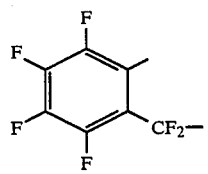

provided that when X is chlorine, no R group can be bromine; and when X is bromine, no R group can be chlorine;

said process being carried out in the presence of a solid catalyst, as charged to the reactor, selected from the class consisting of A. chromium oxide alone or in combination with one or more of Rh°, Ru°, Ir°, Pd°, Pt°, Ag°, phosphorus oxide, silicone oxide, boron oxide or an oxide or halide of aluminum, manganese, zinc, iron, rhodium, nickel, palladium, cobalt, platinum, cerium, silver, coppr, lead bismuth, iridium, magnesium, barium, tin, lanthanum, calcium, ruthenium, iridium, zirconium, vanadium, molybdenum, or tungsten;

B. aluminum oxide in combination with one or more of Rh°, Ru°, Ir°, Pd°, Pt°, Ag°, silicon oxide, phosphorus oxide, boron oxide or an oxide or halide of manganese, zinc, iron, rhodium, nickel, palladium, cobalt, platinum, cerium, silver, copper, lead, bismuth, iridium, magnesium, barium, tin, lanthanum, calcium, ruthenium, iridium, zirconium, vanadium, molybdenum, or tungsten.

2. A process for the disproportionation of a perhaloolefin of the formula

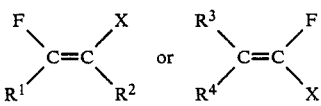

wherein X is chlorine or bromine, and $R^1$, $R^2$, $R^3$ and $R^4$, when each is taken individually, are selected from the class consisting of F, Cl, Br, perfluoroalkyl of 1 to 4 carbon atoms and pentafluorophenyl, and $R^1$ and $R^2$, or $R^3$ and $R^4$, when taken together, are selected from the class consisting of

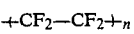

where n=1 or 2 and

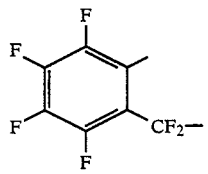

provided that when X is Cl, no R group can be bromine, and when X is Br, no R group can be chlorine; wherein said

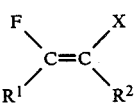

disproportionates to the perhaloolefins

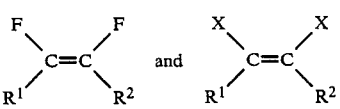

and wherein said

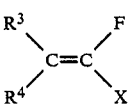

disproportionates to

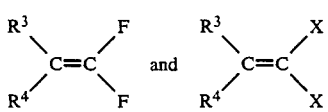

by contacting said

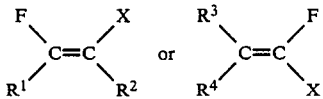

at 90°–400° C. for 0.001–10 seconds, with a solid catalyst, as charged to the reactor, selected from the class consisting of
  A. chromium oxide alone or in combination with one or more of Rh°, Ru°, Ir°, Pd°, Pt°, Ag°, oxide or an oxide or halide of aluminum, mangenese, zinc, iron, rhodium, nickel, palladium, cobalt, platinum, cerium, silver, coppr, lead bismuth, iridium, magnesium, barium, tin, lanthanum, calcium, ruthenium, iridium, zirconium, vanadium, molybdenum, or tungsten;
  B. aluminum oxide in combination with one or more of Rh°, Ru°, Ir°, Pd°, Pt°, Ag°, silicon oxide, phosphorous oxide, boron oxide or an oxide or halide of manganese, zinc, iron, rhodium, nickel, palladium, cobalt, platinum, cerium, silver, copper, lead, bismuth, iridium, magnesium, barium, tin, lanthanum, calcium, ruthenium, iridium, zirconium, vanadium, molybdenum, or tungsten.

3. A process for the conproportionation of

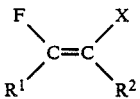

to form

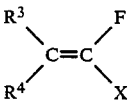

wherein $R^1$ and $R^2$ are defined as in claim 2, using the catalyst and time and temperatures recited in claim 2.

4. A process for the conproportionation of

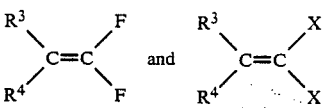

to form $$\begin{array}{c} R^3 \\ \diagdown \\ R^4 \end{array} C = C \begin{array}{c} F \\ \diagup \\ X \end{array}$$

wherein $R^3$ and $R^4$ are defined as in claim 2 using the catalyst and time and temperatures recited in claim 2.

5. A process according to claim 1, 2, 3 or 4, wherein the catalyst is $Cr_2O_3$.

6. A process according to claim 1, 2, 3 or 4 wherein the catalyst is $Cr_2O_3$ supoorted on alumina.

7. A process according to claim 1, 2, 3 or 4 wherein the catalyst is MnO supported on alumina.

* * * * *

UNITED STATES PATENT AND TRADEMARK OFFICE
CERTIFICATE OF CORRECTION

PATENT NO. : 4,814,522
DATED : March 21, 1989
INVENTOR(S) : Frank Julian Weigert It is certified that error appears in the above-identified patent and that said Letters Patent is hereby corrected as shown below:

Claim 2, column 15, line 21, after Ag°, should be inserted

-- phosphorous oxide, silicon oxide, boron --

Signed and Sealed this

Twenty-sixth Day of September, 1989

Attest:

DONALD J. QUIGG

Attesting Officer

Commissioner of Patents and Trademarks